(12) United States Patent
Fridag et al.

(10) Patent No.: US 11,840,506 B2
(45) Date of Patent: Dec. 12, 2023

(54) PROCESS FOR PREPARING $C_5$ ALDEHYDES

(71) Applicant: Evonik Operations GmbH, Essen (DE)

(72) Inventors: Dirk Fridag, Haltern am See (DE); Johannes Knossalla, Gahlen (DE); Alexander Brächer, Haltern am See (DE); Peter Kucmierczyk, Herne (DE); Anna Chiara Sale, Recklinghausen (DE); Robert Franke, Marl (DE); Ana Markovic, Haltern am See (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/310,975

(22) Filed: May 2, 2023

(65) Prior Publication Data
US 2023/0357117 A1    Nov. 9, 2023

(30) Foreign Application Priority Data

May 3, 2022    (EP) ..................................... 22171287

(51) Int. Cl.
| | | |
|---|---|---|
| *C07C 45/50* | (2006.01) | |
| *B01J 31/18* | (2006.01) | |
| *C07C 45/83* | (2006.01) | |

(52) U.S. Cl.
CPC ........... *C07C 45/505* (2013.01); *B01J 31/185* (2013.01); *C07C 45/83* (2013.01)

(58) Field of Classification Search
CPC ....... C07C 45/505; C07C 45/83; B01J 31/185
See application file for complete search history.

(56) References Cited

U.S. PATENT DOCUMENTS

| | | |
|---|---|---|
| 9,272,973 B2 | 3/2016 | Fridag et al. |
| 2015/0224488 A1 | 8/2015 | Fridag et al. |

FOREIGN PATENT DOCUMENTS

| | | |
|---|---|---|
| WO | 2014/056732 | 4/2014 |

OTHER PUBLICATIONS

European Search Report dated Nov. 8, 2022, in European Application No. 22171287.0, 7 pages.

*Primary Examiner* — Sikarl A Witherspoon
(74) *Attorney, Agent, or Firm* — Grüneberg and Myers PLLC

(57) ABSTRACT

A process for preparing $C_5$ aldehydes involves hydroformylation of butenes with synthesis gas in the presence of a homogeneous catalyst system and a solvent. It is a feature of the process that the aldehyde concentration in the reaction mixture is limited.

17 Claims, 1 Drawing Sheet

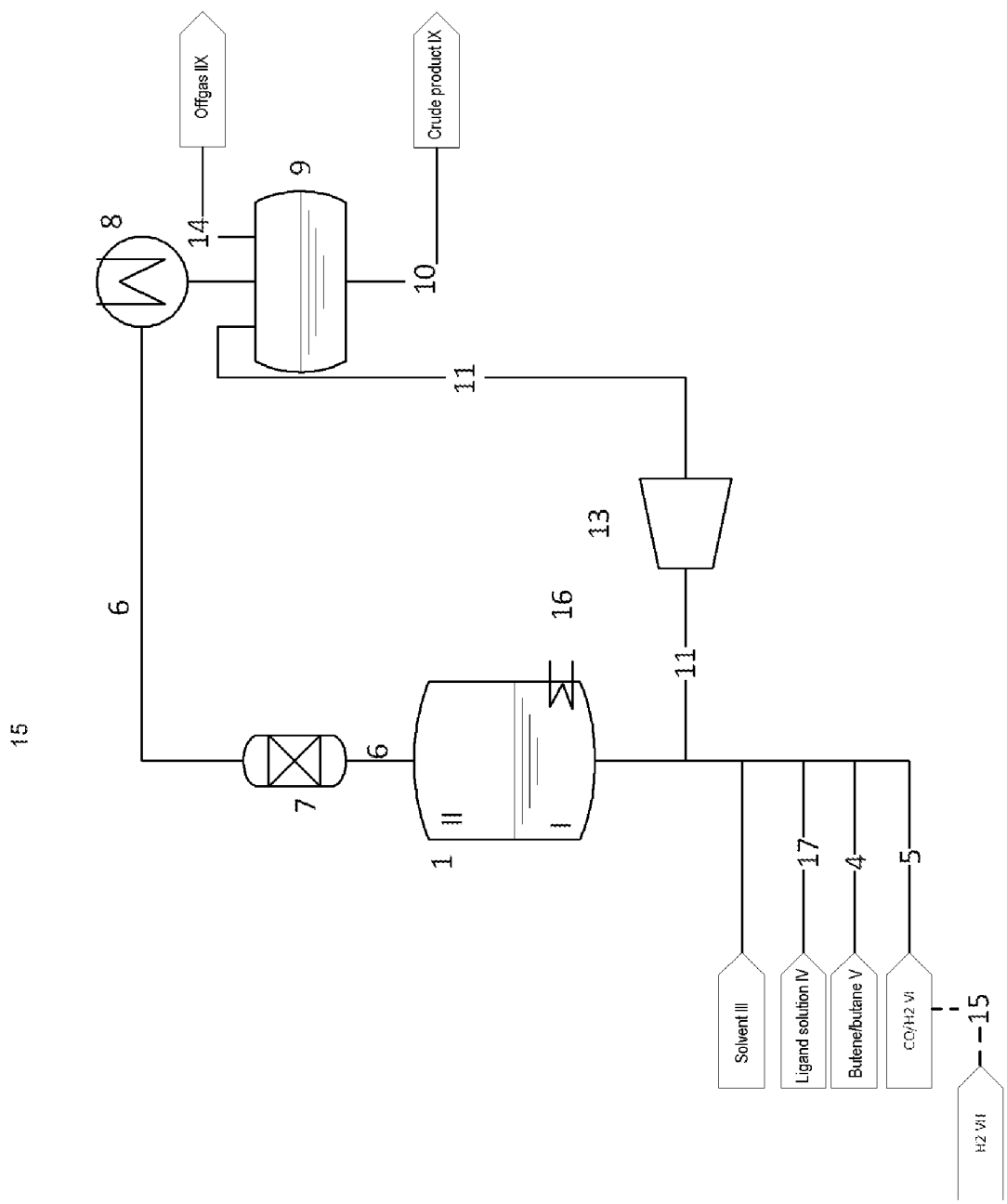

PROCESS FOR PREPARING $C_5$ ALDEHYDES

CROSS-REFERENCE TO RELATED APPLICATIONS

This application claims priority to European Application No. 22171287.0, filed on May 3, 2022, the content of which is hereby incorporated by reference in its entirety.

BACKGROUND OF THE INVENTION

Field of the Invention

The present invention relates to a process for preparing $C_5$ aldehydes by hydroformylation of butenes with synthesis gas in the presence of a homogeneous catalyst system and of a solvent. It is a feature of the process that the aldehyde concentration in the reaction mixture is limited.

Description of Related Art

The hydroformylation of olefins is a known chemical reaction for preparation of aldehydes. The global chemical industry uses hydroformylation reactions produce millions of tonnes of aldehydes annually. In hydroformylation, olefins are reacted with synthesis gas (mixture of CO and $H_2$) to give aldehydes in the presence of a homogeneous catalyst system that may comprise a transition metal, for example rhodium or cobalt, and a ligand.

Some of the hydroformylation processes are conducted as what are called cycle gas processes. In which a gaseous, product-containing output is removed from the reaction zone. Cycle gas processes are typically used for the hydroformylation of relatively short olefins, i.e. olefins having a maximum of 5 carbon atoms, since the aldehydes formed are sufficiently volatile to be able to leave the reaction zone with the gas phase.

The problem with cycle gas processes is that the ligands can be degraded as a result of the conditions that prevail in the hydroformylation. The degradation reactions in which the ligands are destroyed may be various processes, for example hydrolysis, oxidation, Abramov reaction, transesterification, which may also proceed alongside one another. During the hydroformylation, there is then a continuous loss of ligands. In such a case, the ligands must be replenished in a sustained and continuous manner in order to be able to continue to work economically. i.e. with sufficient reaction conversions.

SUMMARY OF THE INVENTION

The problem addressed by the present invention was that of providing a process for hydroformylation in which the degradation reactions of the ligand are reduced or avoided entirely. A further problem addressed by the present invention was that of providing such a process in which no great preparative or chemical-engineering complexity is necessary to achieve the aim, i.e. reduction or avoidance of the degradation reactions of the ligand.

It has been found that, surprisingly, as a result of lowering the aldehyde concentration in the reaction phase, less ligand has to be replenished and the process can nevertheless be performed economically. Degradation reactions of the ligand are clearly reduced.

The problem was solved by a process as described below. Preferred embodiments are also specified in the description below. The present invention accordingly relates to a process for preparing $C_5$ aldehydes by hydroformylation of butenes, in which the butenes are reacted with synthesis gas in at least one reaction zone in the presence of a homogeneous catalyst system and of a solvent, and in which a cycle gas containing at least a portion of the product aldehydes, unconverted butenes and butanes is removed from the reaction zone, characterized in that the aldehyde concentration in the liquid reaction mixture in the reactor is kept below 15% by mass by the cycle gas.

The invention also includes the following embodiments:

1. Process for preparing $C_5$ aldehydes by hydroformylation of butenes, in which the butenes are reacted with synthesis gas in at least one reaction zone in the presence of a homogeneous catalyst system and of a solvent, where a cycle gas containing at least a portion of the product aldehydes, unconverted butenes and butanes is removed from the reaction zone, characterized in that the aldehyde concentration in the liquid reaction mixture in the reactor is kept below 15% by mass by the cycle gas.
2. Process according to embodiment 1, wherein the cycle gas removed from the reaction zone is first directed to an aerosol separator.
3. Process according to embodiment 2, wherein the cycle gas downstream of the aerosol separator is directed to a condenser, by means of which the product aldehydes present in the cycle gas, unconverted butenes and the solvent are condensed out.
4. Process according to embodiment 3, wherein the condensed liquid phase and the gas phase are separated from one another in a phase separator.
5. Process according to embodiment 4, wherein the gas phase is recycled to the reaction zone via a cycle gas compressor.
6. Process according to embodiment 4 or 5, wherein the condensed liquid phase is directed to a $C_4/C_5$ separation consisting of one or more distillation columns.
7. Process according to embodiment 6, wherein the previously removed product aldehydes and the solvent are separated from one another in a solvent removal, and the solvent is recycled to the reactor.
8. Process according to any of embodiments 1 to 7, wherein the solvent has a higher boiling point than the product aldehydes.
9. Process according to any of embodiments 1 to 8, wherein the solvent is INB (isononyl benzoate) or DINCH (diisononyl cyclohexane-1,2-dicarboxylate).
10. Process according to any of embodiments 1 to 9, wherein the hydroformylation in the reaction zone additionally takes place in the presence of a stabilizer.
11. Process according to embodiment 10, wherein the stabilizer is an organic amine compound containing at least one 2,2,6,6-tetramethylpiperidine unit of formula (I):

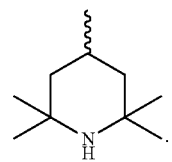

12. Process according to any of embodiments 1 to 11, wherein the homogeneous catalyst system comprises a metal from group 8 or 9 of the Periodic Table of the Elements and at least one organic phosphorus-containing ligand, preferably a mono- or biphosphite ligand.

13. Process according to embodiment 12, wherein the metal is iron, ruthenium, iridium, cobalt or rhodium, preferably cobalt and rhodium.
14. Process according to any of embodiments 1 to 13, wherein the homogeneous catalyst system comprises rhodium and a ligand having the structure of formula (I):

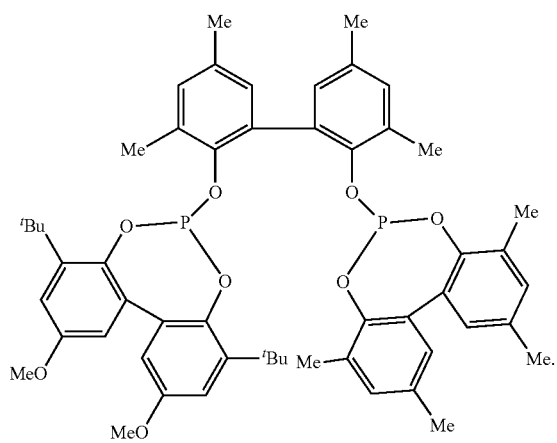

(1)

15. Liquid mixture comprising an aldehyde, cobalt or rhodium, an organic phosphorus-containing ligand and a solvent, wherein the aldehyde concentration in the liquid mixture is below 15% by mass.

BRIEF DESCRIPTION OF THE DRAWING

The FIGURE shows an embodiment of the process according to the Invention.

DETAILED DESCRIPTION OF THE INVENTION

The lowering of the aldehyde concentration is achieved in the context of the present invention by raising the cycle gas rates. In technical terms, however, other measures are also conceivable. Increasing the cycle gas rate can achieve the effect that the product aldehydes formed are removed more quickly from the at least one reaction zone. Moreover, the abovementioned degradation reactions of the ligand are reduced. The process according to the invention can thus be operated such that less ligand has to be replenished compared to conventional processes with similar conversions. The process is thus more resource-sparing than comparable processes. Moreover, costs are saved, which means that the process according to the invention is operable with greater economic viability overall.

Reactants used in the hydroformylation according to the invention are butenes, i.e. linear butenes (n-butenes, i.e. 1-butene and 2-butene) and/or branched butenes (isobutene), which are then reacted with synthesis gas (mixture of CO and $H_2$) in the presence of a homogeneous catalyst to give the desired $C_5$ aldehydes. The butenes to be hydroformylated may be provided as feed mixture for the hydroformylation according to the invention in pure form or in industrially available mixtures. The term "feed mixture" should be understood to relate to any kind of butene-containing mixtures that contain butenes in such an amount as to enable economic operation of hydroformylation. Such feed mixtures contain not only butenes but also the corresponding alkanes, i.e. butanes.

Industrial mixtures that contain butenes and butanes and can be used as feed mixture for the present process are light petroleum fractions from refineries, $C_4$ fractions from FC crackers or steamcrackers, mixtures from Fischer-Tropsch syntheses, mixtures from the dehydrogenation of butanes, and mixtures formed by metathesis or from other industrial processes. Butene mixtures suitable for the process according to the invention may be obtained from the $C_4$ fraction from a steamcracker, for example raffinate I, raffinate II or raffinate III. Another butene-containing mixture that can be used as feed mixture in the present invention Is crude butane. It is also possible to use 1-butene as feed mixture. Butene-containing mixtures that are preferred in accordance with the invention for use as feed mixture are hydrocarbon streams having a butene content of at least 15% by weight. In a preferred embodiment of the present invention, the butene-containing mixtures for use as feed mixture are free of dienes and alkynes, i.e. the content of dienes and alkynes is in each case below 100 ppm, preferably below 10 ppm, more preferably below 1 ppm.

The Inventive hydroformylation of butenes can produce aldehydes having five carbon atoms ($C_5$ aldehydes). The $C_5$ aldehydes include n-pentanal (valeraldehyde), isopentanal (isovaleraldehyde), seo-pentanal (2-methylbutanal) and tert-pentanal (pivalaldehyde). In a preferred embodiment of the present invention, the process described is a process for preparing n-pentanal (valeraldehyde).

The process according to the invention is also conducted using a solvent in which the homogeneous catalyst system is dissolved. At least the solvent and the homogeneous catalyst system dissolved therein form the reaction mixture which is present as liquid phase in the at least one reactor. In a preferred embodiment, the solvent has a higher boiling point than the butenes used and the product aldehydes. Solvents used may be solvents known to the person skilled in the art. Solvents used for the process according to the Invention may especially be INB (Isononyl benzoate) or DINCH (diisononyl cyclohexane-1,2-dicarboxylate).

The catalyst system used in the process according to the invention comprises or consists of a metal from group 8 or 9 of the Periodic Table of the Elements and at least one organic phosphorus-containing ligand. The metal is selected from iron, ruthenium, iridium, cobalt and rhodium. Preferred metals for the catalyst system according to the invention are cobalt and rhodium; particular preference is given to rhodium. Ligands used are preferably mono- or biphosphite ligands, which are known in principle to the person skilled in the art. Suitable ligands are disclosed, for example, in patent applications WO 2017/080690 A1, WD 2014/058732 A1, WO 2014/056735 A1, WD 2014/058736 A1, WD 2014/056737 A1 and DE 10 2008 002 187 A1. A particularly preferred ligand is a compound of the formula (1):

(1)

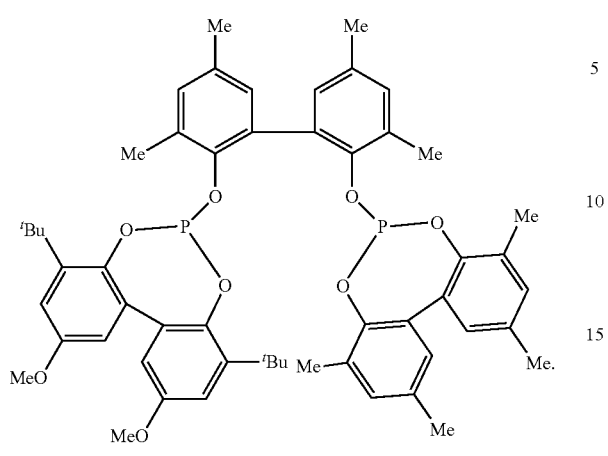

In a particularly preferred embodiment, in the process according to the Invention, a catalyst system comprising rhodium and a ligand of the formula (1) shown above are used.

The molar ratio of rhodium to the mono- or bisphosphite ligands (ligand/rhodium ratio) is preferably within a range from 1 to 100. For every rhodium, there are accordingly 1 to 100 mono- or bisphosphite ligands. The ligand/rhodium ratio is also preferably within a range from 1 to 20, more preferably within a range from 1 to 2. The concentration of rhodium in the liquid reaction mixture is within a range from 1 to 1000 ppm by mass, especially within a range from 20 to 300 ppm by mass and very particularly in the range from 40 to 150 ppm by mass.

The homogeneous catalyst system is preferably not introduced into the process as an active complex ready for use, but is instead prepared in situ, i.e. In the reactor. For this purpose, the active complex is prepared within the at least one reactor in the presence of ligands from rhodium compounds as precursor. Suitable rhodium compounds for this purpose are, for example, rhodium(II) and rhodium(III) salts such as rhodium(III) chloride, rhodium(III) nitrate, rhodium (III) sulfate, potassium rhodium sulfate, rhodium(II) or rhodium(III) carboxylate, rhodium(II) and rhodium(III) acetate, rhodium(II) octanoate, rhodium(II) nonanoate, rhodium(III) oxide, salts of rhodium(III) acid, trisammoniumhexachlororhodate(III). Also suitable are rhodium complexes such as rhodium biscarbonyl acetylacetonate, acetylacetonatobisethylenerhodium(I). Particularly suitable are rhodium acetate, rhodium octanoate and rhodium nonanoate.

In a particularly preferred embodiment of the present invention, the hydroformylation is additionally conducted in the presence of a stabilizer. The stabilizer is preferably an organic amine compound, more preferably an organic amine compound containing at least one 2,2,6,6-tetramethylpiperidine unit of formula (I):

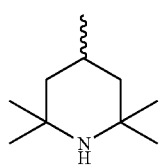

(I)

In a particularly preferred embodiment of the present invention, the stabilizer is selected from the group consisting of the compounds of the following formulae (I.1), (I.2), (I.3), (I.4), (I.5), (I.6), (I.7) and (I.8).

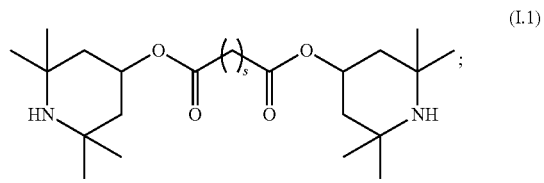

(I.1)

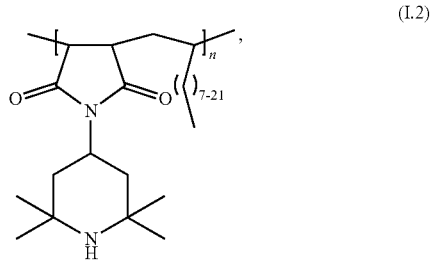

(I.2)

where n is an integer from 1 to 20;

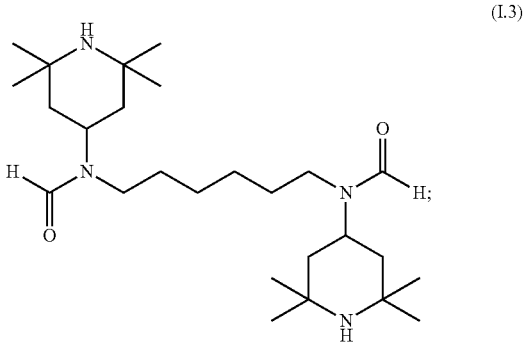

(I.3)

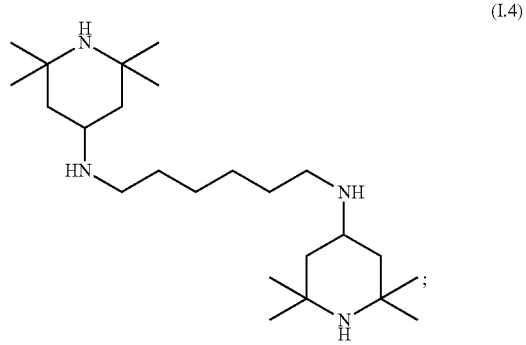

(I.4)

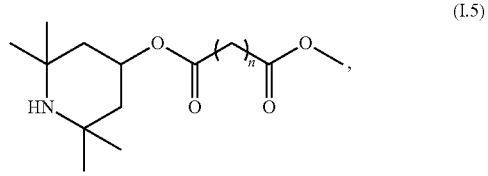

(I.5)

where n is an integer from 1 to 12;

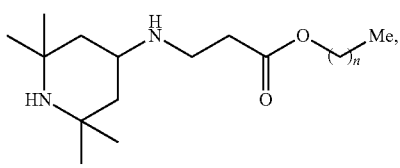

(I.6)

where n is an integer from 1 to 17;

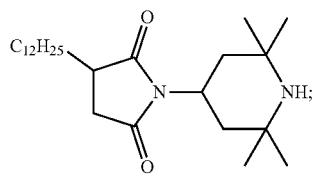

(I.7)

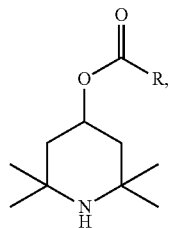

(I.8)

where R is a $C_6$- to $C_{20}$-alkyl group.

Most preferably, the organic amine is a di-4-(2,2,8,6-tetramethylpiperidinyl) sebacate, available, for example, under the Tinuvin® O770 DF brand name. The molar ratio of the ligands to the stabilizer is preferably in the range from 0.1:10 to 10:1, especially within a range from 5:10 to 10:5 and very particularly within a range from 0.8:1 to 1:0.8.

The process according to the present invention is conducted in at least one reaction zone, preferably in a single reaction zone. A reaction zone in the context of the present invention comprises at least one reactor, preferably more than one reactor. The individual reactors within the reaction zone may be connected in parallel or In series. In a particularly preferred embodiment, the reaction zone has at least two reactors connected in parallel.

There is a liquid phase in the at least one reactor that comprises at least the solvent and the homogeneous catalyst system dissolved therein. If a stabilizer is present, this is likewise in the liquid phase in the at least one reactor. The at least one reactor also comprises a gaseous phase. But the reaction takes place in the liquid phase since the catalyst system is also present therein. The reactants, or the feed mixture containing the butenes and butanes, and the synthesis gas are preferably added at the base of the reactor, especially via suitable devices known to the person skilled in the art, such as nozzles. In a particularly preferred embodiment of the present invention, the addition is quantitatively controlled.

The hydroformylation process described here may in principle be conducted continuously or batchwise. But the process is preferably conducted continuously.

The typical conditions in hydroformylation are known to the person skilled in the art. The hydroformylation is conducted preferably at a temperature in the range from 65° C. to 200° C., further preferably at a temperature in the range from 75° C. to 175° C. and more preferably at a temperature in the range from 85° C. to 135° C. The pressure in the hydroformylation is preferably 10 to 200 bar, further preferably 12.5 to 100 bar, more preferably 15 to 25 bar.

As mentioned, in the process according to the invention, a cycle gas containing at least a portion of the product aldehydes, unconverted butenes and butanes is removed from the reaction zone or from the at least one reactor. The cycle gas removed can then be directed to an aerosol separator in order to remove suspended particles of liquid entrained in the cycle gas from the cycle gas. The liquid mixture separated from cycle gas in the aerosol separator may be recycled to the reaction zone or to the reactor(s). The construction and mode of operation of an aerosol separator are familiar to the person skilled in the art. For better deposition of the aerosols, these separators may also be fed with a scrubbing liquid, or corresponding scrubbing columns as likewise familiar to the person skilled in the art may be used.

Downstream of the aerosol separator, the cycle gas may be directed to a condenser, by means of which the product aldehydes present in the cycle gas, the unconverted butene, the butane and the solvent are at least partially condensed out. The condenser is preferably operated at a temperature below the reaction temperature. The temperature in the condenser may be between 30 and 100° C. Particular preference is given to a temperature of 70 to 90° C. The synthesis gas remains in the gas phase and is not condensed out. In that case, what are thus present in the condenser are a liquid phase containing the at least partially condensed constituents, the unconverted butene, the butane and the solvent, and a gas phase comprising the synthesis gas.

The condensed liquid phase and the gas phase may be separated from one another in a phase separator. The resultant gas phase is preferably recycled via a cycle gas compressor to the reaction zone or to the reactor(s). The condensed liquid phase is preferably subjected to a crude product removal, which may consist of one or more distillation columns. This separates the unconverted butenes and butanes (residual $C_4$) from the crude product, which contains at least the aldehydes formed and any high-boiling by-products and/or the solvent. The person skilled in the art is familiar with the conditions for the distillation. The crude product may then be used in downstream reaction steps.

If INB is used as solvent, an additional solvent removal may be advantageous and possibly necessary for the complete removal of the solvent. INB is comparatively volatile, which, in the case of an increase in the cycle gas rate, leads to an increased extent of INB discharge with the cycle gas. However, the INB can lead to problems in downstream process or reaction steps and must therefore be removed. The solvent removal usable for this purpose consists of at least one distillation column. The crude product from the crude product removal is used here, and the solvent and any high-boiling by-products are separated from the $C_5$ aldehydes. The solvent can then be recycled to the reactor. If high-boiling by-products are present, it may be advantageous to provide a purge, i.e. a discharge of a portion of the recyclate, in order not to accumulate high-boiling by-products in the reactor.

It is alternatively possible to provide the crude product removal and the solvent removal in a single distillation column. This is possible, for example, with a dividing wall column, where the residual $C_4$ is obtained at the top, the solvent and any high-boiling by-products are obtained at the bottom, and the $C_5$ aldehydes can be removed in between.

If DINCH is used as solvent, no additional solvent removal is required. DINCH has a higher boiling point and is less volatile than INB. In spite of an increase in the cycle gas rate, at least no more solvent, if any, is discharged with the cycle gas.

In a preferred embodiment, the resultant product aldehyde can be subjected to a downstream reaction step, for example a hydrogenation, an aldolization (aldol condensation), an oxidation to a carboxylic acid or a conversion to the amine.

The present invention further provides a liquid mixture comprising an aldehyde, cobalt or rhodium, an organic phosphorus-containing ligand and a solvent, wherein the aldehyde concentration in the liquid mixture is below 15% by mass. Solvents used may be solvents known to the person skilled in the art. Solvents used for the process according to the invention may especially be INB (isononyl benzoate) or DINCH (diisononyl cyclohexane-1,2-dicarboxylate). Ligands used are preferably phosphoric ester compounds, especially mono- or biphosphite ligands, which are known in principle to the person skilled in the art. Suitable ligands have already been mentioned above and especially mean a ligand of the formula (1). This mixture is especially the liquid reaction mixture from the process according to the invention for preparation or $C_5$ aldehydes.

The FIGURE illustrates the process according to the invention by way of example. The process takes place in a reaction vessel (1) in which there is a liquid reaction phase (I) consisting of solvent and the homogeneously dissolved catalyst system. The reaction vessel (1) also contains a free gas phase (II) and may additionally be heated or cooled by means of an internal heat exchanger (16). Synthesis gas (VI) and reactant (V), i.e. the olefin used or an olefin-containing hydrocarbon stream, are run continuously into the reaction vessel (1), where the reactant (V) may be added either in gaseous or liquid form. It is optionally possible to additionally add hydrogen (VII) to the synthesis gas (VI). In addition, the reaction vessel (1) may be supplied with a ligand solution (IV) and or the solvent (III) in liquid form, in order to compensate for any losses.

Via the cycle gas system, which in this scheme consists of a compressor (13), an aerosol separator (7), a condenser (8), a phase separation vessel (9) and a pipeline system (6, 11) that connects the components of the cycle gas system to one another, a continuous gas stream is removed from the reaction vessel (1). This gas stream is established by the compressor (13) and can be actively varied. The gas stream is directed into the liquid reaction phase (I) from the bottom. The supplied reactant (V) and the synthesis gas (VI) react in the liquid phase to give the corresponding aldehydes. By virtue of their partial pressure, the products formed and unconverted reactants are converted to the gas phase (11) and leave the reaction vessel (1). The gas stream removed is then passed through an aerosol separator (7) in which the entrained fractions of the reaction phase (1) are separated out and returned to the reaction vessel (1). The resultant gas stream then arrives at a downstream condenser (8), where the temperature is lowered to such an extent that the remaining reactants and products are at least partly condensed out of the gas phase. The resultant liquid phase (product-containing) and the gaseous phase are directed together into the phase separation vessel (9). The product-containing liquid phase and gas phase are separated from one another therein. Via the pipeline (10), the liquid crude product (IX) is directed to further workup. The gas phase from the phase separation vessel (9) is directed to the suction side of the compressor (13) and guided back to the reaction vessel (1). The plant pressure can be regulated by means of the offgas (IIX) with the pipeline (14).

The present invention is elucidated hereinbelow with reference to examples. These examples are merely an illustration of the present invention and should not be considered to constitute a restriction.

Example 1 (Non-Inventive)

Before commencement of the reaction, the entire system was inertized with nitrogen and then purged with synthesis gas to free it or nitrogen (less than 5% $N_2$), and then synthesis gas was injected up to 14 bar (abs.). Before commencement, the reaction vessel was charged with a total of about 30 m³ of reaction phase.

This was made up beforehand as follows, 5 m³ of isononyl benzoate (INB) in each case was purged with nitrogen in an inertized batch vessel for 5 h, in order to remove dissolved oxygen. Next, 140 kg of Tinuvin 770DF, 130 kg of ligand having the structure shown in formula (1) and 11 kg of acetylacetonato(dicarbonyl)rhodium(I) were added to the INB via a nitrogen-inertized powder lock. This mixture was heated up to 60° C. and, once the solids had dissolved, the contents were run into the reaction vessel. Monitoring of the ligand concentration in the reaction phase is possible by sampling from the reaction system with subsequent analysis via an HPLC method. In this method, it is likewise possible to determine the oxidized fraction of the ligand. The oxidation fraction was below 10% of the amount of ligand used.

In the next step, the cycle gas compressor was started up. The reaction phase was heated to 120° C. The later reaction pressure of 17 bar (abs.) was established via a control valve in the offgas stream. Excess pressure in the reaction system was dissipated in this way during the heating phase.

On attainment of the reaction temperature, the metered addition of reactant was started at 4500 kg/h. The synthesis gas was run in at a stoichiometric ratio of 1:1.2 to the butene content in the reactant. The reactant used was a $C_4$ stream with a composition of 35% butenes (mixture of 1- and 2-butenes) and 65% n-butane.

The addition of the reactant and the reaction resulted in an increase in the volume of the reaction phase to 50 m³. In order to keep the level constant, the cycle gas was adjusted correspondingly. The proportion of non-complex-bound ligand was determined by regular sampling and analysis by HPLC, and ligand degraded by oxidation was replaced by metered addition of ligands. For this purpose, under inert conditions, the ligand and Tinuvin 770 DF were dissolved in the $C_4$-free crude aldehyde and run into the reaction phase. This kept the ratio between rhodium in the reaction and the unbound ligand constant.

Calculated from the amount of ligand replenished and the mass of aldehyde produced is a ligand use factor in kg of ligand per tonne of aldehyde prepared. The use factor of ligand is calculated as follows:

$$\text{Use of factor of ligand } \frac{\text{kg}}{t} = \frac{\text{Mass of ligand metered in as pure substance in kg}}{\text{Mass of aldehyde produced in } t}$$

This is equated to 100% under these conditions in this example, and serves as a reference for Example 2. At the same time, the aldehyde content in the reaction solution was determined from the sample by means of gas chromatography analysis. On average, the aldehyde content was 15% by mass.

The number of moles of aldehyde prepared per hour and number of moles of butenes used per hour were additionally used to calculate the yield by the following formula: A yield of 80% was established.

$y$ aldehydes=mol/$h$ aldehydes in condensed output from plant/mol/$h$ butenes in feed to plant−mol/$h$ butenes in condensed output from plant Example 2 (Inventive)

The experiment was set up and commenced analogously to Example 1. However, the cycle gas rate was run such that the aldehyde concentration in the reaction phase was on average 13%. Level losses were compensated for by replenishing solvent, INB in this case.

Analogously to Example 1, in this example too, the proportions of the free ligand and the yield were determined. As was also the case in Example 1, the ligand use factor in kg per tonne of aldehyde prepared is determined. The ligand use factor was only 75% based on Example 1. There is an overview of the data ascertained in Table 1.

TABLE 1

Overview of the reaction data

|  | Example 1 (non-inventive) | Example 2 (inventive) |
|---|---|---|
| Use factor | 100% | 75% |
| Aldehyde concentration in the reaction phase | 15% | 13% |
| Yield | 60% | 55% |

The invention claimed is:

1. A process for preparing $C_5$ aldehydes by hydroformylation of butenes, the process comprising:
   reacting the butenes with synthesis gas in at least one reaction zone of a reactor, in the presence of a homogeneous catalyst system and of a solvent, wherein a cycle gas containing at least a portion of product aldehydes, unconverted butenes, and butanes is removed from the at least one reaction zone, and
   wherein an aldehyde concentration in a liquid reaction mixture in the reactor is kept below 15% by mass by the cycle gas.

2. The process according to claim 1, wherein the cycle gas removed from the at least one reaction zone is first directed to an aerosol separator.

3. The process according to claim 2, wherein the cycle gas downstream of the aerosol separator is directed to a condenser, wherein the product aldehydes present in the cycle gas, the unconverted butenes, and the solvent are condensed out.

4. The process according to claim 3, wherein a condensed liquid phase and a gas phase are separated from one another in a phase separator.

5. The process according to claim 4, wherein the gas phase is recycled to the at least one reaction zone via a cycle gas compressor.

6. The process according to claim 4, wherein the condensed liquid phase is directed to a $C_4/C_5$ separation consisting of one or more distillation columns.

7. The process according to claim 6, wherein previously removed product aldehydes and the solvent are separated from one another in a solvent removal, and the solvent is recycled to the reactor.

8. The process according to claim 1, wherein the solvent has a higher boiling point than the product aldehydes.

9. The process according to claim 1, wherein the solvent is isononyl benzoate (INB) or diisononyl cyclohexane-1,2-dicarboxylate (DINCH).

10. The process according to claim 1, wherein the hydroformylation in the at least one reaction zone additionally takes place in the presence of a stabilizer.

11. The process according to claim 10, wherein the stabilizer is an organic amine compound containing at least one 2,2,8,8-tetramethylpiperidine unit of formula (I):

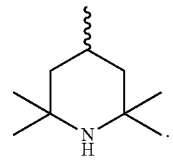

12. The process according to claim 1, wherein the homogeneous catalyst system comprises a metal from group 8 or 9 of the Periodic Table of the Elements, and at least one organic phosphorus-containing ligand.

13. The process according to claim 12, wherein the metal is iron, ruthenium, iridium, cobalt, or rhodium.

14. The process according to claim 1, wherein the homogeneous catalyst system comprises rhodium and a ligand having the structure of formula (1):

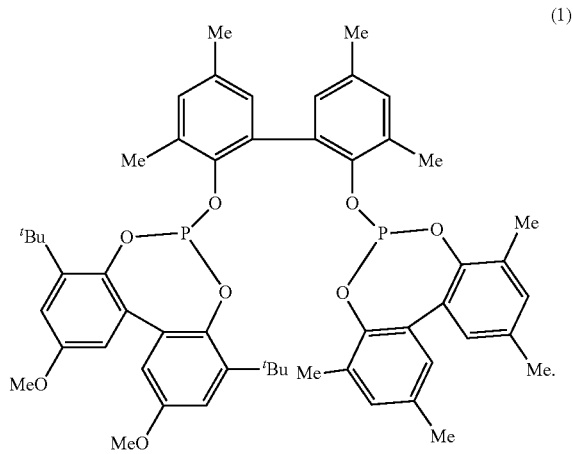 [SMILES: COc1cc(C(C)(C)C)c2op(Oc3c(C)cc(C)cc3-c3cc(C)cc(C)c3Op3oc4c(C)cc(C)cc4c4cc(C)cc(C)c4o3)oc3c(C(C)(C)C)cc(OC)cc3c2c1]

15. A liquid mixture, comprising:
    an aldehyde,
    cobalt or rhodium,
    an organic phosphorus-containing ligand, and
    a solvent,
    wherein an aldehyde concentration in the liquid mixture is below 15% by mass.

16. The process according to claim 12, wherein the at least one organic phosphorus-containing ligand is a mono- or biphosphate ligand.

17. The process according to claim 13, wherein the metal is cobalt or rhodium.

* * * * *